US012692324B2

(12) United States Patent
Chang et al.

(10) Patent No.: US 12,692,324 B2
(45) Date of Patent: Jul. 28, 2026

(54) ANTI-CHITINASE-3-LIKE PROTEIN-1 (YKL-40) NEUTRALIZING ANTIBODY AND USES THEREOF

(71) Applicant: Institute of Nuclear Energy Research, Atomic Energy Council, Executive Yuan, R.O.C, Taoyuan (TW)

(72) Inventors: Ming-Cheng Chang, Taoyuan (TW); Ping-Fang Chiang, Taoyuan (TW); Yu-Jen Kuo, Taoyuan (TW)

(73) Assignee: Institute of Nuclear Energy Research, Atomic Energy Council, Executive Yuan, . R.O.C, Taoyuan (TW)

( * ) Notice: Subject to any disclaimer, the term of this patent is extended or adjusted under 35 U.S.C. 154(b) by 743 days.

(21) Appl. No.: 18/302,869

(22) Filed: Apr. 19, 2023

(65) Prior Publication Data

US 2024/0132621 A1 Apr. 25, 2024
US 2024/0228663 A9 Jul. 11, 2024

(30) Foreign Application Priority Data

Oct. 24, 2022 (TW) ................................. 111140288

(51) Int. Cl.
| | |
|---|---|
| *C07K 16/40* | (2006.01) |
| *A61K 51/04* | (2006.01) |
| *A61P 35/00* | (2006.01) |
| *A61K 39/00* | (2006.01) |

(52) U.S. Cl.
CPC .......... *C07K 16/40* (2013.01); *A61K 51/0497* (2013.01); *A61P 35/00* (2018.01); *A61K 2039/505* (2013.01); *C07K 2317/565* (2013.01); *C07K 2317/76* (2013.01)

(58) Field of Classification Search
None
See application file for complete search history.

(56) References Cited

U.S. PATENT DOCUMENTS

2019/0062457 A1* 2/2019 Elias ....................... A61P 35/04

OTHER PUBLICATIONS

Darr et al., The Role of YKL-40 in Predicting Resistance to Docetaxel Chemotherapy in Prostate Cancer, Urologia Internationalis, Karger, 2018, 101: 65-73.
Kirwan et al., Glycosylation-Based Serum Biomarkers for Cancer Diagnostics and Prognostics, Biomed Res Int, 2015, 490531.
(Continued)

*Primary Examiner* — Aurora M Fontainhas
*Assistant Examiner* — Tirone D. Johnson
(74) *Attorney, Agent, or Firm* — Troutman Pepper Locke LLP; Tim Tingkang Xia, Esq.

(57) ABSTRACT

Disclosed herein an isolated neutralizing antibody, which is capable of specifically binding to chitinase-3-like protein-1 (YKL-40) and uses thereof. The neutralizing antibody can further conjugate with a metal chelator to form an antibody complex. Further, labeling the antibody complex with a radioactive metal nuclide results in formation of a radioactive antibody complex, which can be used as a contrast agent and treatment for YKL-40 over-expression-related diseases. The radioactive antibody complex can specifically bind to YKL-40, and can be used for diagnosis and the preparation of the use of the treatment for cancers related to YKL-40 over-expression.

19 Claims, 7 Drawing Sheets
Specification includes a Sequence Listing.

YKL-40 on cell membrane

(56) References Cited

OTHER PUBLICATIONS

Kjaergaard et al., Observational and genetic plasma YKL-40 and cancer in 96,099 individuals from the general population, Int J Cancer, 2015, 137: 2696-2704.

Yun et al., Dysregulation of cancer genes by recurrent intergenic fusions, Genome Biol., 2020, 21: 166.

Chiang et al., Overexpression of CHI3L1 is associated with chemoresistance and poor outcome of epithelial ovarian carcinoma, Oncotarget, 2015, 6, 37.

Lin et al., CHI3L1 results in poor outcome of ovarian cancer by promoting properties of stem-like cells, Endocrine-Related Cancer, 2019, 26, 73-88.

Chang et la., Develop companion radiopharmaceutical YKL40 antibodies as potential theranostic agents for epithelial ovarian cancer, Biomedicine & Pharmacotherapy, 2022, 155, 113668.

* cited by examiner

Days
(After treated with Lu-177-DTPA-YKL-40
antibody complex)

ANTI-CHITINASE-3-LIKE PROTEIN-1 (YKL-40) NEUTRALIZING ANTIBODY AND USES THEREOF

CROSS REFERENCE TO RELATED APPLICATION

All related applications are incorporated by reference. The present application is based on, and claims priority from, Taiwan Application Ser. No. 111140288, filed on Oct. 24, 2022, the disclosure of which is hereby incorporated by reference herein in its entirety.

The sequence information contained in the Sequence Listing XML file, with the file name "307US2_Sequence.xml" created on Apr. 14, 2023 and having a file size of 12,602 bytes, is incorporated by reference herein in its entirety.

TECHNICAL FIELD

The present invention relates to an isolated neutralizing antibody specifically binding to chitinase-3-like protein-1 (YKL-40), wherein the isolated neutralizing antibody is capable of forming an antibody complex with a metal chelator and can be applied to the imaging and treatment of cancers related to highly expressing YKL-40.

BACKGROUND

Chitinase-3-like protein-1 (CHI3L1) gene is located on chromosome 1q32.1, and its protein product-YKL-40 (or YKL-40), which is a 40-kDa glycoprotein secreted by various cells in human tissues, such as chondrocytes, synovial membrane cells, vascular endothelial cells, inflammatory cells, macrophages and cancer cells. The function of YKL-40 is to participate in the process of cell proliferation and differentiation, apoptosis, angiogenesis, inflammation, and tissue remodeling. Many of the cancer patients are found to possess an increasing detected value of chitinase-3-like protein-1 (YKL-40) in the serum, including breast cancer, gastrointestinal cancer, liver cancer, prostate cancer, brain cancer, astrocytoma, endometrial cancer, and lung cancer (Dan et al., 2018, Urol Int 101: 65-73.; Kirwan et al., 2015, Biomed Res Int 2015: 390531.; Kjaergaard et al., 2015, Int J Cancer 137: 2696-2704.; Yun et al., 2020, Genome Biol 21: 166).

In previous studies, it was also found that the ovarian cancer patients with high expression of chitinase-3-like protein-1 in their ovarian cancer tissues had a poor prognosis. Therefore, chitinase-3-like protein-1 can be used as a clinical prognostic indicator for ovarian cancer patients. In addition, chitinase-3-like protein-1 also has an important impact on the generation of ovarian cancer stem cells. Chitinase-3-like protein-1 can promote β-catenin and SOX2 protein expression by regulating the signal transmission pathways of Akt and Erk, and endows ovarian cancer cells with the properties of cancer stem cells (Chiang et al., 2015, Oncotarget 6: 39740-39755.; Lin et al., 2019, Cancer 26: 73-88.). It is therefore that chitinase-3-like protein-1 plays a very important role in the early development and metastasis of ovarian cancer or other cancers.

Traditionally, the standard treatment for ovarian cancer is tumor debulking surgery and adjuvant chemotherapy. However, in addition to killing cancer cells, these treatments are also harmful to healthy cells. Although the initial response of ovarian cancer patients to treatment can reach 80% of all epithelial ovarian cancer patients, only 40-60% in advanced patients. Most patients will relapse within two years, however, the resistances to chemotherapy drugs play an important role in tumor recurrence and progression. The most important problem in treating ovarian cancer is that when the ovarian cancer spreads beyond the pelvic cavity or the ovarian cancer recurs, a second surgery will be applied as the treatment. However, the treatment is often ineffective, and a chemotherapy is also required after the surgery. Most of the treatments fail to result in obvious effectiveness, and patients barely have follow-up treatment strategies either. If the therapeutic drugs and the accompanying early diagnosis tools can be developed for advanced ovarian cancer, we can accurately select target cells for specific treatment. This will be a potential strategy for precision medical treatment.

In the previous studies, the antibodies developed against YKL-40 failed to make breakthroughs due to low specificity and lack of tumor growth inhibitory effect. In view of this, the inventors of the present disclosure optimized (recombinant) the protein sequence of the original YKL-40 antibody and modified the antigen recognition region to enhance the specific binding ability with YKL-40. Further, after conjugating with the metal chelating group, the conjugated antibody complex (or the antibody complex) is then labeled with a radioactive metal nuclide such as lutetium-177 (Lu-177) and actinium-225 (Ac-225) and serves as a targeted radiotherapy antibody drug for ovarian cancer or other cancers overexpressing YKL-40 providing more effective therapy for cancer patients.

SUMMARY

In one embodiment of the present disclosure, an isolated neutralizing antibody capable of specifically binding to chitinase-3-like protein-1 (hereinafter referred to as YKL-40) is provided, wherein the isolated neutralizing antibody comprises heavy chain CDR1, CDR2, CDR3 domains and light chain CDR1, CDR2, CDR3 domains; wherein the amino acid sequences of heavy chain CDR1, CDR2, and CDR3 domains respectively comprise GYTFPNYGMN (SEQ ID NO: 1), WINTYTGEPTYTVDFKG (SEQ ID NO: 2) and ARSFYGTNGFDY (SEQ ID NO: 3); wherein the amino acid sequences of light chain CDR1, CDR2, and CDR3 domains respectively comprise KASENVGTYVS (SEQ ID NO: 4), GASNRYI (SEQ ID NO: 5) and GQSYS-YPPT (SEQ ID NO: 6).

In one embodiment of the present disclosure, an isolated neutralizing antibody capable of specifically binding to YKL-40 is provided, comprising a heavy chain variable region (VH) and a light chain variable region (VL), wherein the heavy chain variable region comprises the amino acid sequence of SEQ ID NO: 7, and the light chain variable is region (VL) comprises the amino acid sequence of SEQ ID NO: 8.

In one embodiment of the present disclosure provides a nuclide acid encoding the isolated neutralizing antibody that specifically binds to YKL-40, a vector comprising the nucleic acid molecule, a host cell comprising the vector.

In one embodiment of the present disclosure, an antibody complex is provided, which is formed by complexing the isolated neutralizing antibody capable of specifically binding to YKL-40 with a metal chelating group (referred to YKL-40 neutralizing antibody complex or antibody complex). In some embodiments, the metal chelating group is 1,4,7-triazacyclononane-N,N',N"-triacetic acid (NOTA), 1,4,7,10-tetraazacyclododecane-1,4,7,10-tetraacetic acid (DOTA), tetraazacyclododecane-1-ethyl, or diethylenetri-aminepentaacetic acid (DTPA), 1,4,8,11-tetraazacyclotetradecane-N,N',N'',N'''-tetraacetic acid (TETA), 1,4,7-triazacy-clononane phosphinic acid (TRAP), or ethylenediaminetetraacetic acid (EDTA). In another embodiment, the metal chelating group is diethylenetri-aminepentaacetic acid (DTPA).

In one embodiment of the present disclosure, an antibody complex is provided, which is formed by complexing the isolated neutralizing antibody capable of specifically binding to YKL-40 with a metal chelating group, wherein the antibody complex further comprising a radioactive metal nuclide, labeling on the antibody complex. In some embodiments, the radioactive metal nuclide is indium-111 (In-111), lutetium-177 (Lu-177), actinium-225 (Ac-225), gallium-68 (Ga-68), gallium-67 (Ga-67), yttrium-90 (Y-90), or copper-64 (Cu-64). In one embodiment, the radioactive metal nuclide is indium-111 (In-111). In another embodiment, the radioactive metal nuclide is lutetium-177 (Lu-177). In another embodiment, the radioactive metal nuclide is actinium-225 (Ac-225).

In one embodiment of the present disclosure provides a contrast agent comprising the antibody complex and a contrast excipient.

In one embodiment of the present disclosure provides a pharmaceutical composition comprising the antibody complex, and a use of the antibody complex in the preparation of medicines for diagnosing or treating diseases related to overexpression of YKL-40. In some embodiments, the disease is a cancer and is selected from the group consisting of breast cancer, liver cancer, prostate cancer, brain cancer, astrocytoma, ovarian cancer, endometrial cancer, lung cancer or gastrointestinal cancer. In another embodiment, the disease is epithelial ovarian cancer.

Those ordinarily skilled in the art of the present disclosure can fully understand the concept of the present disclosure, the adopted methodology and the implementation concepts after referring to the following embodiments.

BRIEF DESCRIPTION OF THE DRAWINGS

To make the foregoing and other objects, features, advantages, and examples of the present invention more comprehensibly, the drawings are described as follows.

4

Figure 6:
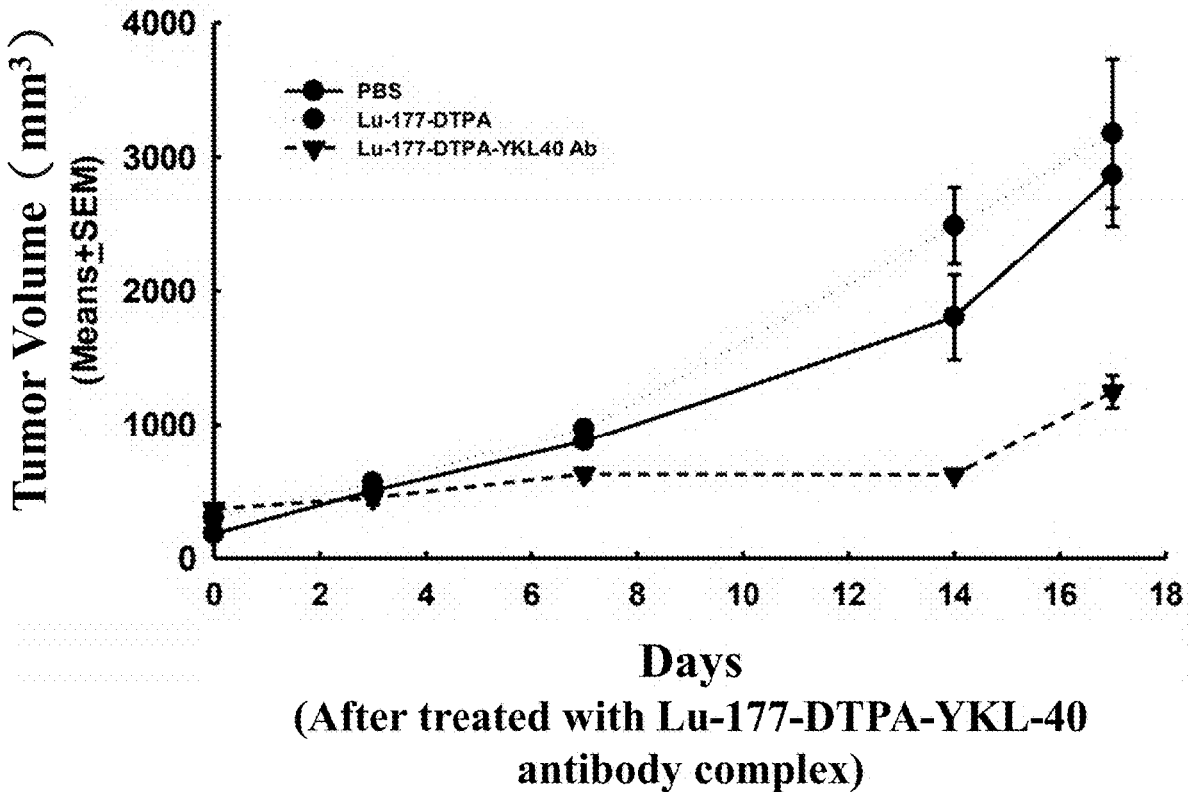

FIG. 6 represents the results of the treatment to tumor-bearing mice using the YKL-40 neutralizing antibody complex of the disclosure after labeling with lutetium-177 (Lu-177).

DETAILED DESCRIPTION

To make the description of the present disclosure more detailed and complete, the following provides an illustrative text description of the implementations and specific examples of the present invention; but the implementations and specific examples of the present invention are not limited thereto.

The term "individual" or "patient" refers to an animal capable of receiving the antibody, the antibody complex, or the isotopic labeled antibody complex of the present invention. In a preferable implementation, the animal is a mammal, and in particular, is a human.

"Chitinase-3-like protein-1" in the present disclosure refers to the protein product of the chitinase-3-like protein-1 (CHI3L1) gene-YKL-40, which is a 40-kDa glycoprotein. The YKL-40 used in the present disclosure is a recombinant YKL-40 obtained by gene recombination in which the inventor optimized the amino acid sequence of the antibody binding site of the original YKL-40. In the YKL-40 neutralizing antibody system described in the present disclosure, the anti-recombinant YKL-40 neutralizing antibody is obtained by using the above-mentioned recombinant YKL-40 as an antigen, and in the following examples of the present disclosure refer as YKL-40 neutralizing antibody or anti-YKL-40 neutralizing antibody.

The term "disease" herein refers to a disease associated with a high expression or overexpression of YKL-40. Specifically, the expression of YKL-40 in the disease symptoms will be significantly higher than the expression level of normal cells, which can be used as an indicator to identify the existence of the diseases. For example, the "disease" may be a tumor associated with a high expression or overexpression of YKL-40.

The "cancer" may be a non-solid tumor or a solid tumor. For example, the cancer includes, but not limited to breast cancer, liver cancer, prostate cancer, brain cancer, astrocytoma, ovarian cancer, endometrial cancer, lung cancer, gastrointestinal cancer or epithelial ovarian cancer which highly expresses YKL-40.

The "recombinant human antibody" described in the specification includes preparation, expression, producing or isolation of human antibodies by recombinant techniques which are familiar to those skilled in the art. For example, including the antibodies obtained by gene transfection of human immunoglobulin genes, or isolated from the hybridoma prepared from human immunoglobulin genes; the antibodies obtained by expression, producing or isolation by applying insertion of other DNA sequences into human immunoglobulin gene sequences; antibodies obtained by using recombinant or combined human antibodies. The obtained recombinant human antibody contains the variable region and the constant region with specific protein sequence, and the variable region contains recombinant gene codes which endow it having the specific binding ability to the foreign antigen.

The "isolated antibody" described in the specification means an antibody purified from a mixture containing other components in the environment in which the antibody was produced.

The "nucleic acid molecule" described in the specification includes DNA and RNA molecules, and the nucleic acid molecules can be single-stranded or double-stranded, purified or non-purified and other forms.

The "vector" described in the specification is a form known to those skilled in the art to express the DNA to be manipulated, such as a form that is connected to the DNA to be manipulated to form a double-stranded DNA circle. The vector can express the DNA to be manipulated after being introduced into the host cell.

The "complex" described in the specification represents the combination of two or more molecules, which can be covalent or non-covalent, one molecule to one molecule, one molecule to multiple molecules, or multiple molecules to multiple molecules. The combination can be at a specific binding region or a non-specific binding region in the molecular structure.

The "antibody complex" described in the specification represents the antibody complex formed by combining antibody molecules with molecules such as drug molecules and/or metal chelating groups in a one-to-one or one-to-many or many-to-many form. For example, an antibody molecule can directly bind to one or more drug molecules or metal chelating group molecules, and an antibody molecule can directly bind to one or more drug molecules and metal chelating group molecules. Those skilled in the art can also combine the above-mentioned antibody with drug molecules and/or metal chelating group molecules through one or more linker molecules without affecting the binding ability of the antibody to bind to the antigen without undue experimentation.

The term "about", as described in this specification, generally means that an actual value falls within plus or minus 10%, 5%, 1%, or 0.5% of a specific value or range. The term "about" herein means that an actual value falls within an acceptable standard error of an average value, depending on the consideration of a person of ordinary skill in the art the present invention pertains. Except for experiment examples, or unless otherwise clearly stated, it should be understood that the ranges, quantities, numerical values, and percentages used herein are all modified by "about". Therefore, unless otherwise stated, the values or parameters disclosed in this specification and the appended claims are all approximate values, and may be changed as required.

Unless otherwise stated, the scientific and technical terms used in this specification have the same meanings as those understood and commonly used by a person of ordinary skill in the art. In addition, nouns used in this specification include the singular and plural forms of the nouns, unless otherwise specified.

In order to solve the problems in the prior art, the inventors of the present disclosure optimized the protein sequence of the original YKL-40 antibody by modifying its antigen recognition region to enhance the specific binding ability to YKL-40. It can also be used as antibody-drug complex to provide targeted radiotherapy for ovarian cancer or other cancers that overexpress YKL-40 by further conjugating the antibody with a metal chelating group to form an antibody complex, and then labeling the complex with radioactive nuclide such as lutetium-177 (Lu-177) or actinium-225 (Ac-225) to provide a more effective therapy for cancer patients.

The present disclosure provides an isolated neutralizing antibody capable of specifically binding to chitinase-3-like protein-1 (YKL-40), which comprises heavy chain CDR1, CDR2, and CDR3; light chain CDR1, CDR2, and CDR3; wherein the amino acid sequences of the heavy chain CDR1, CDR2, and CDR3 respectively comprise GYTFPNYGMN (SEQ ID NO: 1), WINTYTGEPTYTVDFKG (SEQ ID NO: 2) and ARSFYGTNGFDY (SEQ ID NO: 3); and the amino acid sequences of the light chain CDR1, CDR2, and CDR3 respectively comprise KASENVGTYVS (SEQ ID NO: 4), GASNRYI (SEQ ID NO: 5) and GQSYSYPPT (SEQ ID NO: 6). Each of the amino acid sequence is shown in TABLE 1:

TABLE 1

| SEQ ID NO | CDRs | Amino Acid Sequence |
|---|---|---|
| SEQ ID NO: 1 | VH CDR1 | GYTFPNYGMN |
| SEQ ID NO: 2 | VH CDR2 | WINTYTGEPTYTVDFKG |
| SEQ ID NO: 3 | VH CDR3 | ARSFYGTNGFDY |
| SEQ ID NO: 4 | VL CDR1 | KASENVGTYVS |
| SEQ ID NO: 5 | VL CDR2 | GASNRYI |
| SEQ ID NO: 6 | VL CDR3 | GQSYSYPPT |

In one embodiment of the present disclosure, the isolated neutralizing antibody capable of specifically binding to YKL-40 comprises a heavy chain variable region (VH) and a light chain variable region (VL), wherein the heavy chain variable region comprises the amino acid sequence of SEQ ID NO: 7, and the light chain variable region (VL) comprises the amino acid sequence of SEQ ID NO: 8, as shown in TABLE 2 below:

TABLE 2

| SEQ ID NO | Amino Acid Sequence |
|---|---|
| SEQ ID NO: 7 (VH) | QIQLVQSGPELKKPGETVRISCKASGYTFPNYGMNWVKQAPGKGLK WMGWINTYTGEPTYTVDFKGQFAFSLETSASTAYLQINNLKNEDTAT YFCARSFYGTNGFDYWGQGTTLTVSS |
| SEQ ID NO: 8 (VL) | NIVMTQSPKSMSMSVGERVTLSCKASENVGTYVSWYQQKPEQSPKL VIYGASNRYIGVPDRFTGSGSATDFTLTISSVEAEDLADYHCGQSYSY PPTFGGGTKLEIK |

In one embodiment of the disclosure provides a nucleic acid molecule encoding an amino acid sequence comprising an isolated neutralizing antibody capable of specifically binding to YKL-40. For example, in one embodiment, the isolated neutralizing antibody comprising the amino acid sequences of the heavy chain CDR1, CDR2, and CDR3 domains and the light chain CDR1, CDR2, and CDR3 domains of the YKL-40 neutralizing antibody, wherein the amino acid sequences of the heavy chain CDR1, CDR2, and CDR3 domains respectively comprise GYTFPNYGMN (SEQ ID NO: 1), WINTYTGEPTYTVDFKG (SEQ ID NO: 2) and ARSFYGTNGFDY (SEQ ID NO: 3); the amino acid sequence of the light chain CDR1, CDR2, and CDR3 domains respectively comprise KASENVGTYVS (SEQ ID NO: 4), GASNRYI (SEQ ID NO: 5) and GQSYSYPPT (SEQ ID NO: 6). In another embodiment, a vector comprising the nucleic acid molecule, or a host cell comprising the vector is provided.

The YKL-40 neutralizing antibody system described in this embodiment is produced by Genedirex Biotechnology Company, and its production method is a regular technique known to those skilled in the art for the production of recombinant human antibodies. For example, taking 5 µg/mL of recombinant human chitinase-3-like protein-1 (YKL-40) optimized by the inventor of the present disclosure and then injecting it into an experimental animal to stimulate the immune response of the host animal. Then the serum of the experimental animal after immunization is collected and used to perform the extracellular test of the inhibition of IL-8 secretion and the expression of phosphorylated AKT, so as to confirm the activity of the antibody in the obtained animal serum. When the serum of experimental animal is confirmed to significantly inhibit the secretion of IL-8 and phosphorylation of AKT, it is then selected for further producing the hybridomas. Then use YKL-40 to screen positive hybridomas by Enzyme-linked immunosorbent assay (ELISA), and then use immunoblot (Western blot) method to select the candidate strain with the highest binding activity to produce YKL-40 neutralizing antibody, and use Affi-Gel® AMAPS® II kit (Bio-Rad, Hercules, CA) to isolate and purify anti-YKL-40 neutralizing antibody, or YKL-40 neutralizing antibody.

The disclosed YKL-40 neutralizing antibody is analyzed by flow cytometry for its binding ability to human ovarian cancer cell CA5171, and the results show that the YKL-40 neutralizing antibody represents a stronger binding ability to CA5171 ovarian cells than the control group (using IgG antibody).

The disclosed YKL-40 neutralizing antibody is also analyzed by flow cytometry to see if it can induce the apoptosis of human ovarian cancer cell CA5171, and the results show that YKL-40 neutralizing antibody did not induce the apoptosis of human ovarian cancer cell CA5171. In addition, the YKL-40 neutralizing antibody was not observed to be cytotoxic under the conditions of the examples disclosed in the present disclosure either.

In one embodiment, the YKL-40 neutralizing antibody of the present disclosure can effectively conjugate with a metal chelating group to form an antibody complex. The antibody complex can be further labeled with a radioactive metal nuclide and applied to SPECT/CT diagnostic imaging or used as radiotherapy drugs.

In one embodiment, the YKL-40 antibody complex of the disclosure is labeled with a radioactive metal nuclide and injected into animals exhibiting ovarian cancer tumor, then followed by SPECT/CT imaging examination. The results confirm that the disclosed antibody complex can effectively accumulate in the tumor site. In another embodiment, the antibody complex of the present disclosure is labeled with a radioactive metal nuclide and injected into animals exhibiting ovarian cancer tumor for radiotherapy experiments. The results show that after radiotherapy, the tumor volume is significantly smaller than that without treatment. Experimental results show that the YKL-40 antibody complex of the present disclosure can significantly inhibit tumor growth, and can be used as a medicine for diagnosing or treating related diseases that highly express YKL-40.

The following examples illustrate the various implementations and results of the present disclosure in conjunction with the figures for those ordinarily skilled in art of the present disclosure to understand and exercise the technical methodology of the disclosure, and obtain the expected results as the disclosure of the description. Thus, the embodiments disclosed below shall not be viewed as to limit the scope of the present invention.

Figures 1A, 1B:
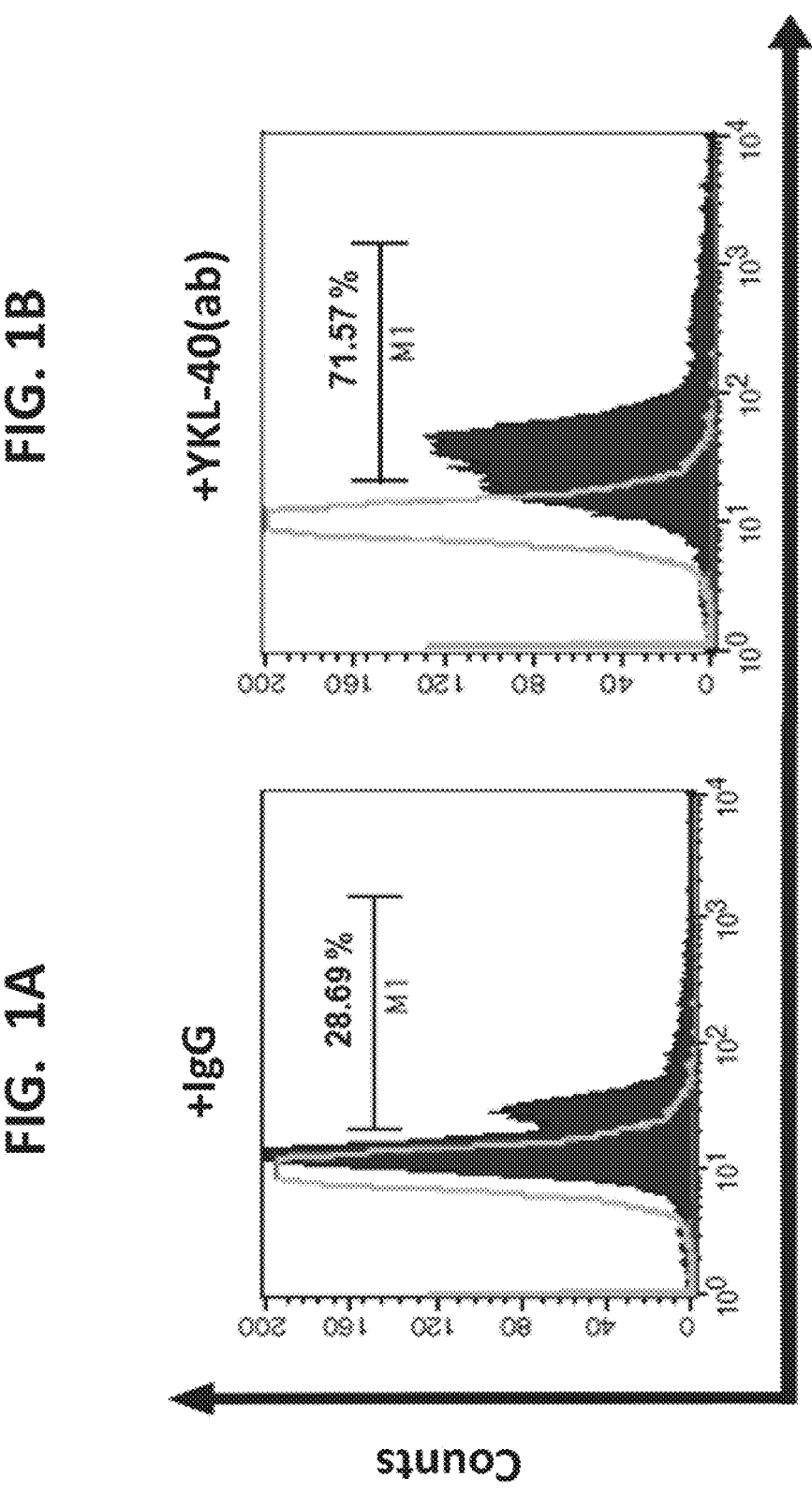
FIGS. 1A and 1B represent the results of measuring the binding ability of human ovarian cancer cell CA5171 with the YKL-40 neutralizing antibody provided in the present disclosure by flow cytometry.

EXAMPLE 1: Binding Ability Analysis of YKL-40 Neutralizing Antibody Binding with Human Ovarian Cell When the YKL-40 neutralizing antibody of the present disclosure is isolated and purified, its binding ability to human ovarian cell CA5171 is then evaluated by flow cytometry. In this example, the antibody of the control group and YKL-40 neutralizing antibody are respectively added to the culture of the ovarian cell CA5171. After a period of culturing, the human ovarian cell CA5171 are then analyzed by flow cytometry. Please refer to FIGS. 1A and 1B. FIG. 1A shows the analysis results of the binding ability of the control group antibody (IgG) binding with human ovarian cell CA5171. FIG. 1B shows the analysis results of the binding ability of the YKL-40 neutralizing antibody binding with human ovarian cell CA5171. From the results, the binding ability of the control group antibody IgG is 28.69%, while the binding ability of the YKL-40 neutralizing antibody is as high as 71.57%. The results clearly indicate that the YKL-40 neutralizing antibody of the present disclosure can significantly bind to human ovarian cancer cell CA5171.

EXAMPLE 2: The Analysis of YKL-40 Neutralizing Antibody Inducing Human Ovarian Cell Apoptosis It is important to know whether the YKL-40 neutralizing antibody of the present disclosure can induce cell apoptosis after combining with human ovarian cell CA5171. In this experiment, two specific dyes "7-amino-actinomycin D" (7-AAD) and "Annexin V" are used in the flow cytometry analysis to detect if the YKL-40 neutralizing antibody induces the cell apoptosis. In addition, the combination treatment of the chemotherapy drug paclitaxel and the YKL-40 neutralizing antibody is also analyzed in this experiment.

Figure 2A:
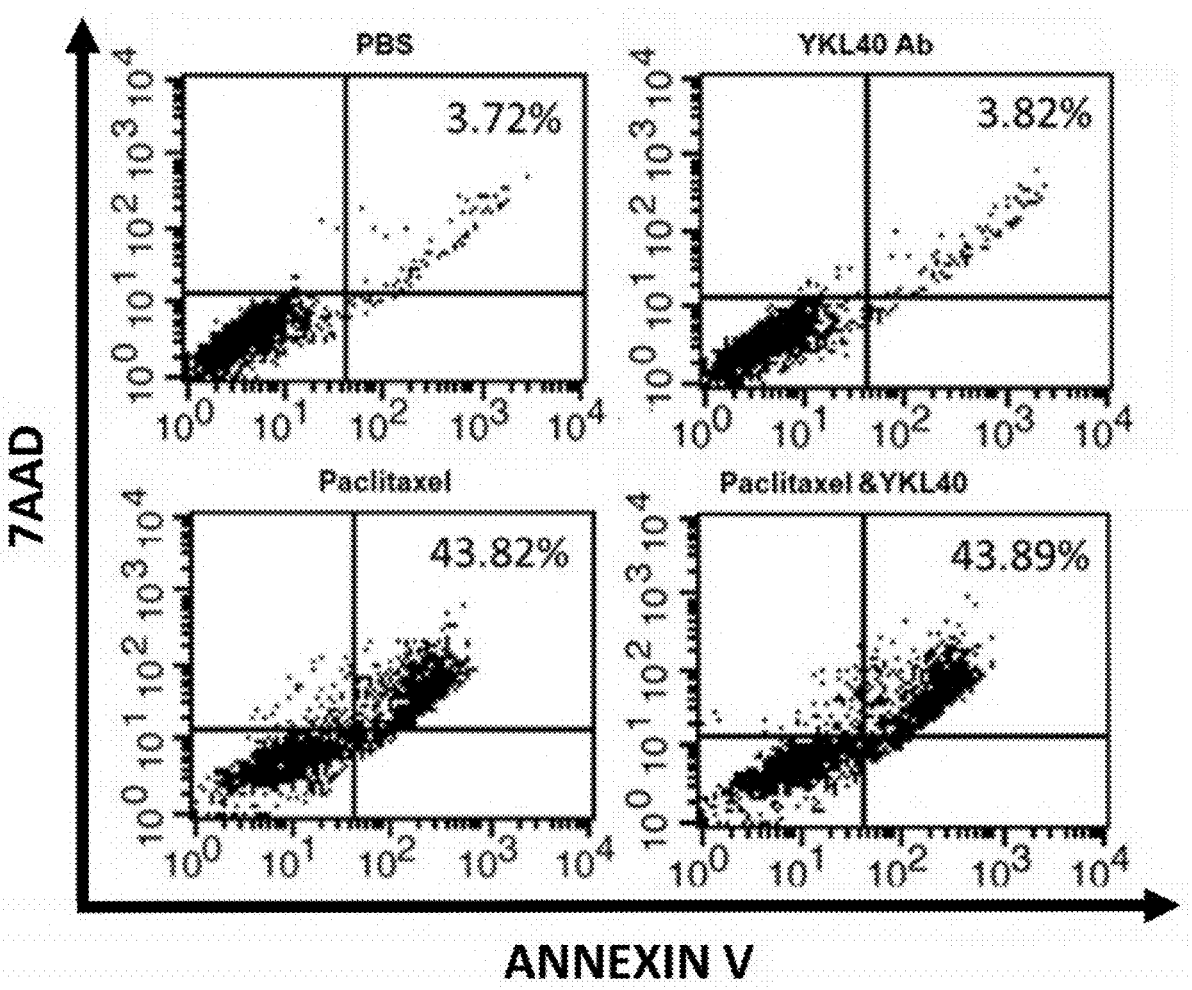
FIGS. 2A and 2B represent the results of analyzing the ability of the YKL-40 neutralizing antibody and/or the chemotherapeutic drug paclitaxel to induce apoptosis of human ovarian cancer cell CA5171 cells by flow cytometry.
Figure 2B:
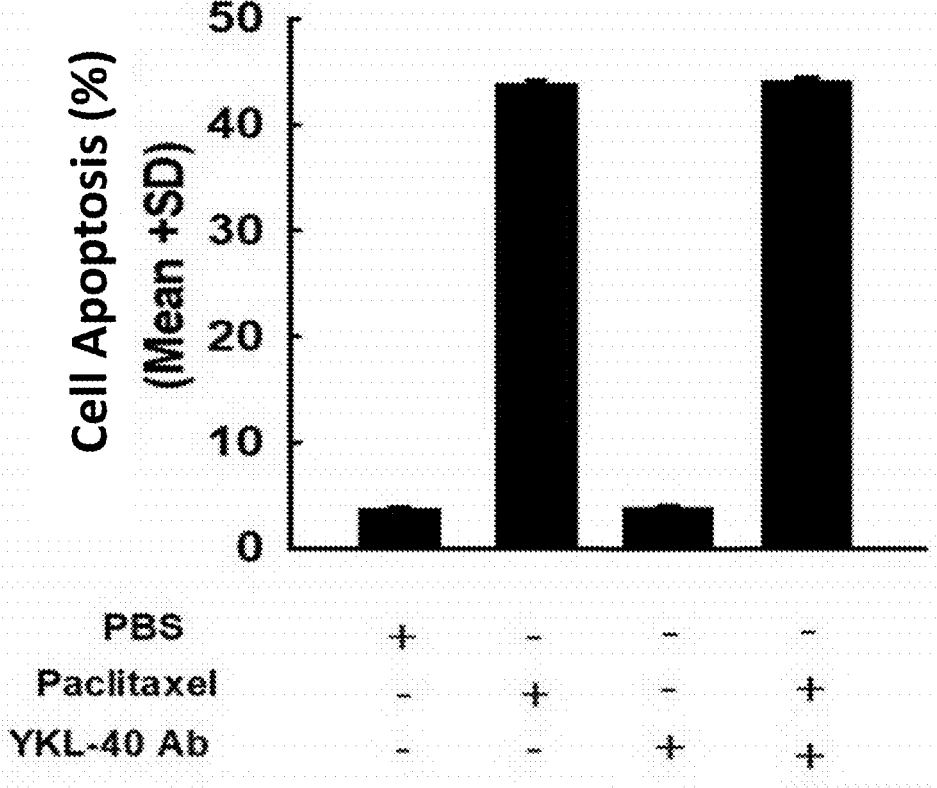

The experiment procedure applied herein is, firstly, to treat human ovarian cancer cell CA5171 with a final concentration of 50 µg/mL YKL-40 neutralizing antibody and/or 2.5 nM paclitaxel, then culture them at 37° C. for 48 hours. The control group is treated with normal saline. After the culturing, the cells are collected and stained with 7-AAD and FITC-conjugated annexin V (FITC, Fluorescein isothiocyanate) dyes for 30 minutes. After staining, the cells are washed by using cytometer analysis solution (normal saline with a final concentration of 0.2% fetal bovine serum and 0.5% sodium azide), and then analyzed by flow cytometry. The data is then collected and analyzed by CellQuest software, and the experiment results are shown in FIGS. 2A and 2B. FIG. 2A is the raw data obtained by the flow cytometer, and FIG. 2B is the analyzed result by CellQuest software in this embodiment. In the results, the proportion of Annexin V/7-ADD-positive apoptosis in human ovarian cancer cell CA5171 is $3.79\pm0.15\%$ in the control group added with normal saline, while in the treatment group added with YKL-40 neutralizing antibody is $3.91\pm0.11\%$. There is no significant increase observed in cell apoptosis. In addition, the group treated with both paclitaxel and YKL-40 neutralizing antibody, the proportion of AnnexinV/7-AAD-positive cell apoptosis in human ovarian cancer cell CA5171 is 44.22±0.28%, while in the group treated with paclitaxel alone is 43.90%±0.35%. The combined treatment of paclitaxel and YKL-40 neutralizing antibody does not significantly increase human ovarian cancer cell apoptosis. The experiment results clearly indicate that YKL-40 neutralizing antibody does not induce the apoptosis of ovarian cancer cell CA5171. In addition, the cytotoxicity of YKL-40 neutralizing antibody does not increase when combined with paclitaxel chemotherapeutic drug.

EXAMPLE 3: Labeling YKL-40 Neutralizing Antibody Complex with a Radioactive Metal Nuclide For applying the YKL-40 neutralizing antibody of the present disclosure to cancer diagnosis and treatment, the YKL-40 neutralizing antibody of the disclosure is further conjugated with a metal chelating group to form a YKL-40 neutralizing antibody complex (antibody complex). The antibody complex is then labeled with a radioactive metal nuclide, and thus can be used as a medication for the diagnosis and treatment of diseases related to the high expression or overexpression of YKL-40.

YKL-40 neutralizing antibody can be used to conjugate with metal chelating groups commonly used in this field, which include: 1,4,7-triazacyclononane-N,N',N"-triacetic acid (NOTA), 1,4,7,10-tetraazacyclododecane-1,4,7,10-tetraacetic acid (DOTA), tetraazacyclododecane-1-ethyl, diethylene Diethylenetriaminepentaacetic acid (DTPA), 1,4, 8,11-tetraazacyclotetradecane-N,N',N",N"'-tetraacetic acid (TETA), 1,4,7-triazacyclononane phosphinic acid (TRAP), or ethylenediaminetetraacetic acid (EDTA). The methods of conjugating antibodies or proteins with the above metal chelating groups are known to those skilled in the art (Morals M. et al., 2018, Drug Discov Today Technol. p.91-104). In this embodiment, as an example, YKL-40 neutralizing antibody is used to conjugated with DTPA to form a DTPA-YKL-40 antibody complex. First, the YKL-40 neutralizing antibody is mixed with the chelator p-SCN-Bn-DTPA in 0.1 M carbonate-bicarbonate buffer (pH 8.4). The molar ratio for the chelator and the antibody is higher than 25 to 1. The amount of the chelating agent used in this step can be varied from situations. For example, the amount of chelating agent used can be, in molarity, 50-fold higher than that of YKL-40 neutralizing antibody in order to increase the molecular number of the chelating group bound to the antibody. The reaction mixture is incubated on the shaker at 4° C. overnight, and then, by using Vivaspin ultrafiltration concentrator, centrifuge the sample to purify and to perform the buffer exchange to desalt and concentrate the antibody complex. Wash the bound DTPA-YKL-40 antibody complex three times with phosphate buffered saline, and centrifuge at 14,000 g for 10-20 minutes at 4° C. to remove unbound p-SCN-Bn-DTPA. At last, rinse with an appropriate amount of normal saline, and suck out the liquid remaining in Vivaspin. The purity of the obtained product is then analyzed by thin layer chromatography (TLC). If the purity of the obtained product is higher than 90%, it can be used for the subsequent experiments. If the purity is below 90%, applied a 50 kDa cut-off filter to further purify the obtained product until the purity is higher than 90%.

Label with a Radioactive Metal Nuclide: Indium-111, Lutetium-177

The detail procedure of labeling protein drugs with radioactive metal nuclide indium-111 (In-111) can refer to the published literature Shih, Y. H. et al., 2015, Oncotarget 6: 16601-16610. The procedure for labeling the YKL-40 neutralizing antibody of the disclosure with radioactive metal nuclide lutetium-177 (Lu-177) is similar to that described in the above-mentioned literature. In brief, firstly, dissolve the purchased lutetium-177 (Lu-177) in 0.1M hydrochloric acid in a final volume 1 mL. Then, dissolve the DTPA-conjugated YKL-40 antibody complex (DTPA-YKL-40 antibody complex) in a dimethyl sulfoxide (DMSO) solution at a concentration of 20 μg/μL. Next, take 1 μL of DTPA-YKL-40 antibody complex and admix it with 82.5 MBq 177LuCl 3 in 1M anhydrous sodium acetate (pH 4.0) solution to a final volume of 600 μL. Afterwards, incubate the admixture for 30 minutes at 37° C. and 500 rpm condition, and then use Vivaspin® (Sartorius, Goettingen, Germany) to remove the unbound lutetium-177 (Lu-177) and purify the labeled radioactive antibody complex. Finally, the diafiltration cup of Vivaspin® is removed, and the radioactive antibody complex Lu-177-DTPA-YKL-40 is recovered, concentrated and purified by normal saline. In this example, the specific activity of the lutetium-177-DTPA-YKL-40 antibody complex must be higher than 4.1 GBq/mg for use.

Figure 3A:
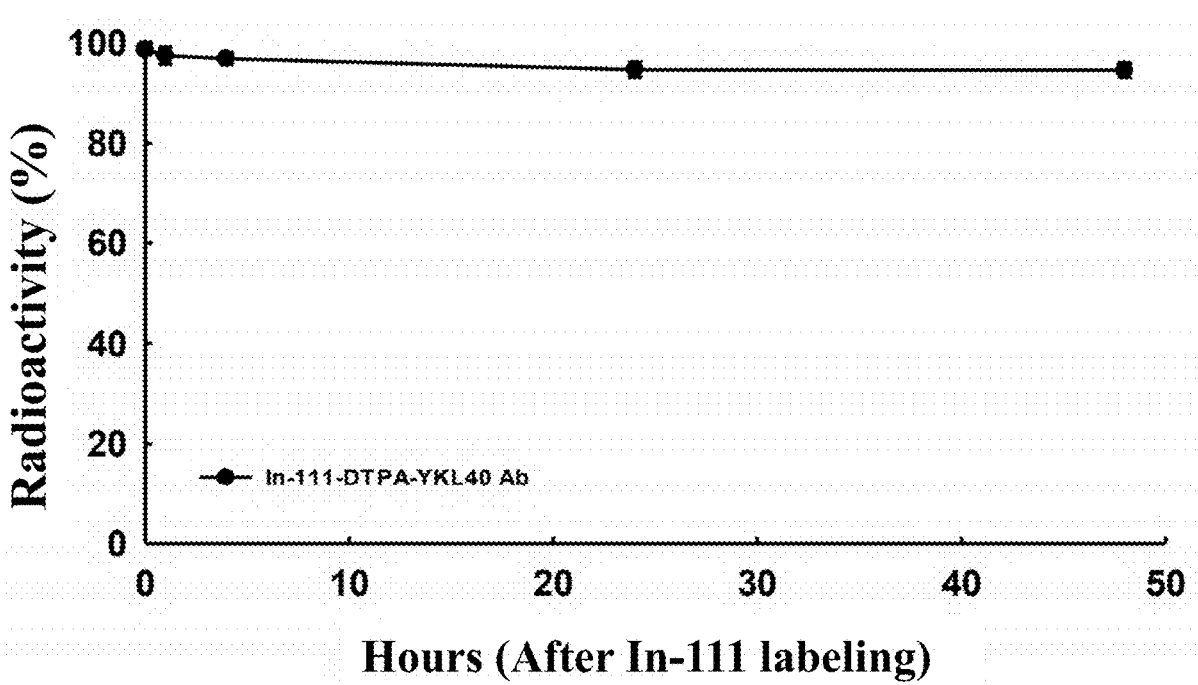
FIGS. 3A and 3B represent the analysis of drug stability and biological stability of the YKL-40 neutralizing antibody complexes of the present disclosure by using real-time thin-layer chromatography (TLC) after labeling with indium-111 (In-111).
Figure 4A:
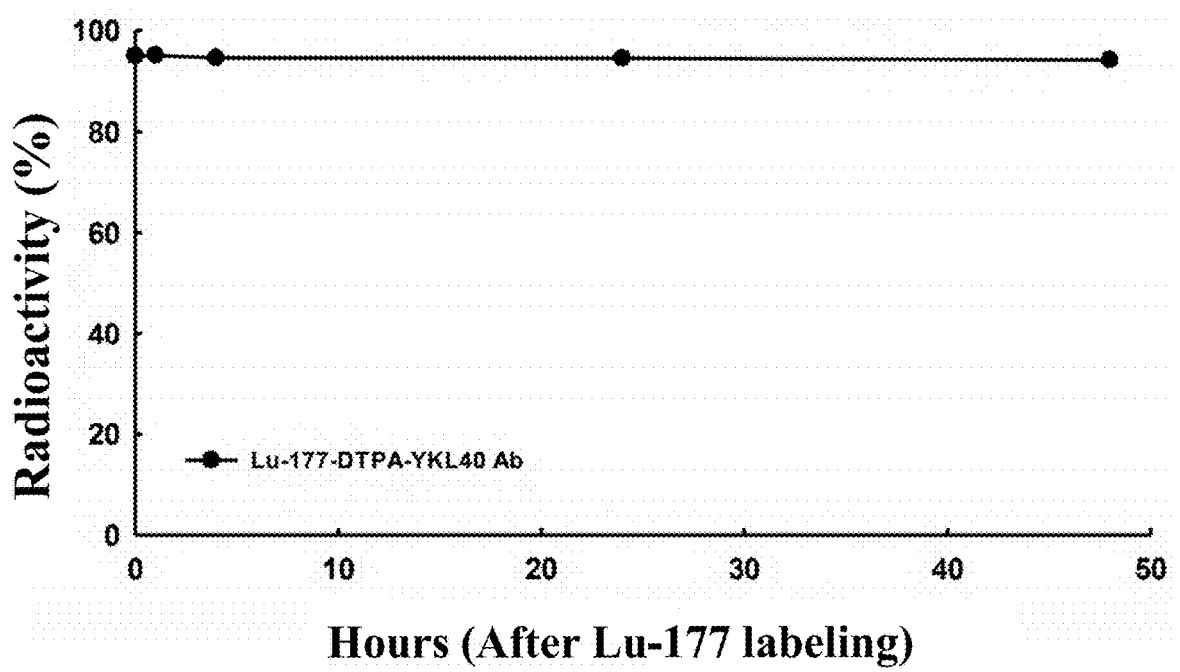
FIGS. 4A and 4B represent the analysis of drug stability and biological stability of YKL-40 neutralizing antibody complexes of the present disclosure by using real-time thin-layer chromatography (TLC) after labeling with lutetium-177 (Lu-177).

Drug Stability and Biological Stability Analysis of Radiolabeled Antibody Complexes In one embodiment of the present disclosure, when the antibody complex DTPA-YKL-40 is labeled with the radioactive metal nuclide indium-111 (In-111) or lutetium-177 (Lu-177), the drug stability and biological stability of the radiolabeled antibody complexes have to be analyzed. The drug stability analyses are performed by keeping the radiolabeled antibody complex samples in normal saline at 4° C., and then, take a part of the sample out after standing for 0, 4, 24 and 48 hours respectively. Perform real-time thin-layer chromatography to analyze the radioactive purity of the samples. The drug stability analysis results of the DTPA-YKL-40 antibody complex labeled with indium-111 (In-111) or lutetium-177 (177) are shown in FIGS. 3A and 4A respectively, and in TABLE 3 below.

TABLE 3

| Nuclide | Time | | | | |
| | 0 hr | 1 hr | 4 hrs | 24 hrs | 48 hrs |
| --- | --- | --- | --- | --- | --- |
| In-111 | 98.6 ± 1.0% | 97.4 ± 1.7% | 96.8 ± 1.1% | 94.6 ± 1.5% | 94.5 ± 1.4% |
| Lu-177 | 95.0 ± 0.2% | 95.1 ± 0% | 94.6 ± 0.3% | 94.5 ± 0.2% | 94.2 ± 0.1% |

The above results indicate that the DTPA-YKL-40 antibody complex labeled with indium-111 (In-111) or lutetium-177 (Lu-177) retains more than 90% of the radioactivity even after 48 hours.

Figure 3B:
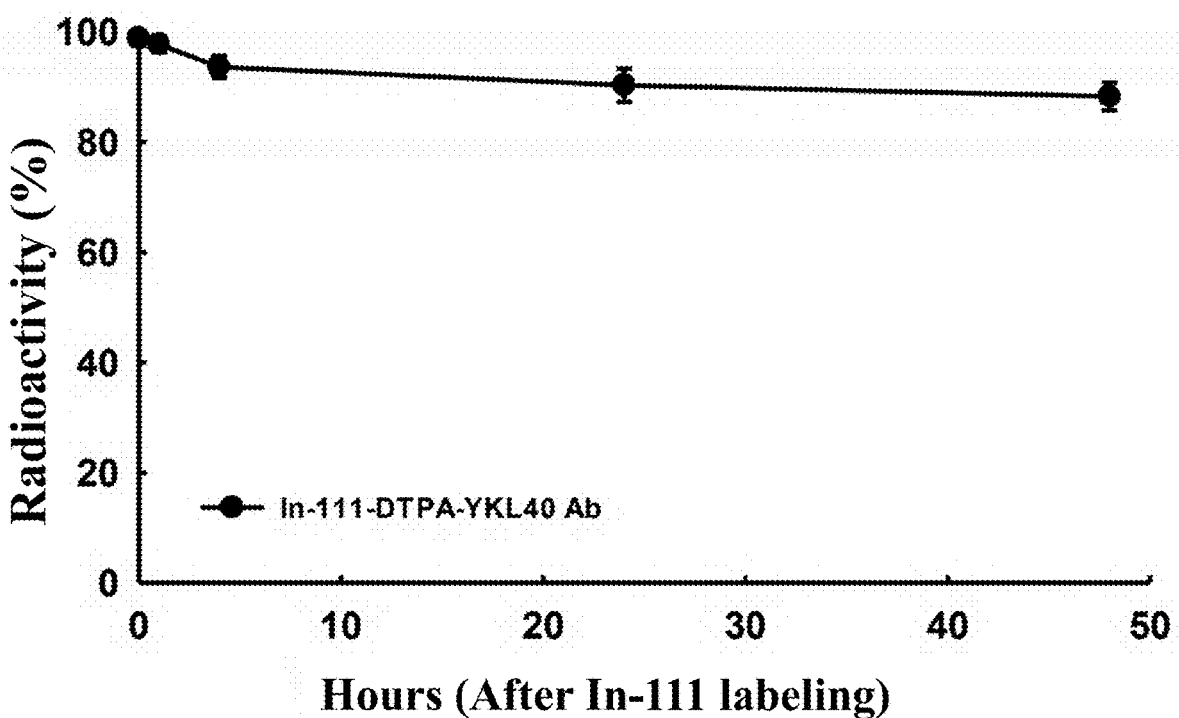
Figure 4B:
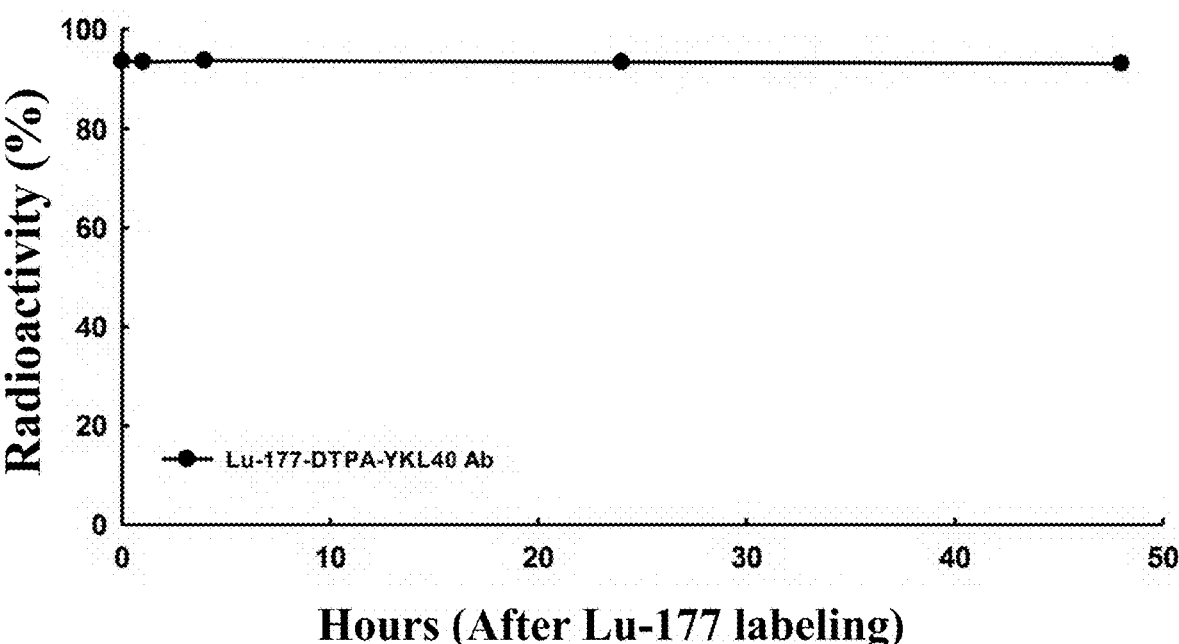

Furthermore, it is important to understand if the antibody complexes of the present disclosure undergo degradation while interacting with enzymes such as proteases under physiological conditions containing serum, and result in drug instability. Thus, the biological stability of the radiolabeled antibody complexes of the present disclosure are examined. The radiolabeled antibody complex samples are kept at 37° C. in the presence of serum. Then after standing for 0, 4, 24, and 48 hours, take a part of the sample out respectively, and analyze the radioactive purity of the samples by real-time thin-layer chromatography. The biological stability analysis results of the DTPA-YKL-40 antibody complex labeled with indium-111 or lutetium-177 are shown in FIGS. 3B and 4B respectively, and in TABLE 4 below.

TABLE 4

| Nuclide | Time | | | | |
|---|---|---|---|---|---|
| | 0 hr | 1 hr | 4 hrs | 24 hrs | 48 hrs |
| In-111 | 98.8 ± 1.1% | 97.7 ± 0.7% | 93.6 ± 1.3% | 90.3 ± 2.2% | 88.3 ± 2.8% |
| Lu-177 | 93.6 ± 0.2% | 93.4 ± 0.1% | 93.7 ± 0.4% | 93.4 ± 0.2% | 93.1 ± 0.2% |

The results unveiled above demonstratively indicate that the DTPA-YKL-40 antibody complex of the present disclosure, radioactively labeled with indium-111 or lutetium-177, can possess a considerable proportion (~90%) of radioactive activity even after 48 hours being stored at 4° C. of storage condition or at 37° C. of physiological condition. The results clearly show that the radioactively labeled DTPA-YKL-40 antibody complex possesses a relevantly stable biological stability and is suitable for radiotherapy applications.

EXAMPLE 4: Nano SPECT/CT Bioimaging Experiment

Figure 5A:
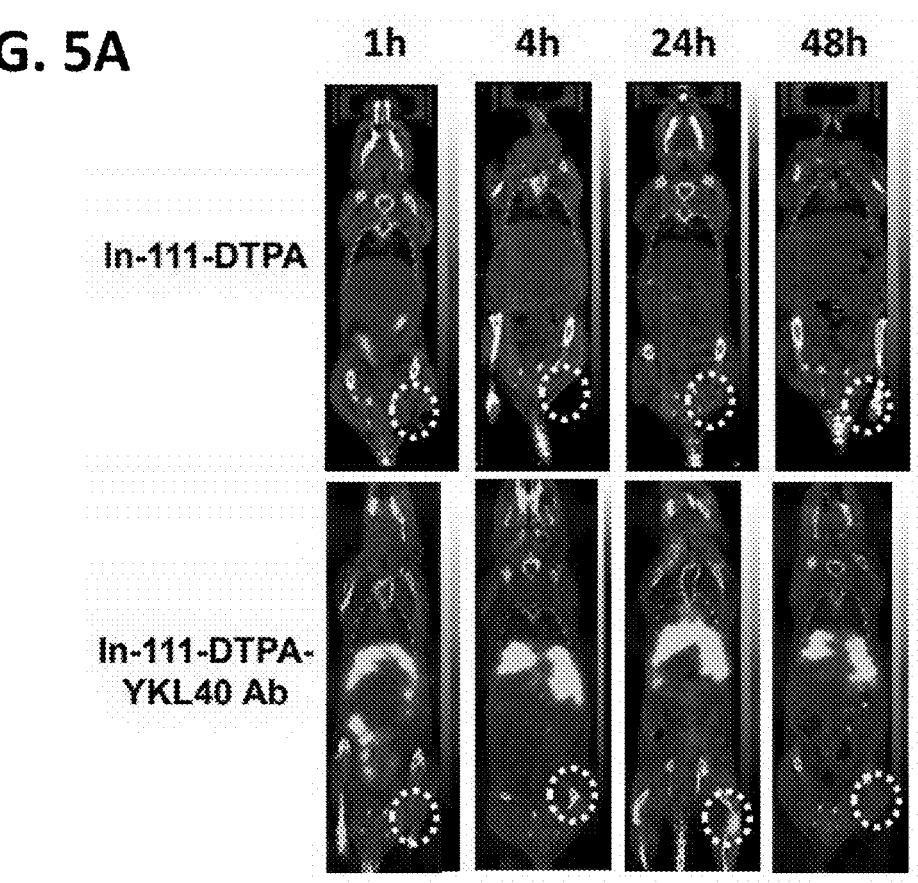
FIGS. 5A and 5B represent the results of the biological distribution analysis of the YKL-40 neutralizing antibody complex of the disclosure in an orthotopic ovarian cancer animal model after labeling with indium-111 (In-111)by using Nano SPECT/CT bioimaging.

The experiment results have revealed that the radiolabeled antibody complexes of the present disclosure possess appreciable drug stability and biological stability. In order to verify these research results in a tumor-carried animal model, the CA5171 ovarian cancer cells, which overexpress chitinase-3-like protein-1, are inoculated in the left hind limb of the experiment animals. After the tumor volume grow to 200-300 mm3, use indium-111-DTPA-YKL-40 antibody complex as a radio-diagnostic drug for tumor mapping. The method of administration of diagnostic drugs is to inject the indium-111-DTPA-YKL-40 antibody complex by tail vein injection. Three tumor-carried mice are used as the animal model in both control and treatment groups, and the cross-sections of transverse, sagittal, and coronal are then taken at different time points such as 1, 4, 24 and 48 hours after administration. The tumor-carried mice of the control group are injected with indium-111-DTPA only, without YKL-40 antibody complex. The results are shown in FIG. 5A. FIG. 5A shows the comparison of Nano SPECT and CT fusion images at different time points to observe the accumulation of radio-diagnostic drugs with/without DTPA-YKL-40 antibody complex, in tumor tissue. The experiment results show that when the experimental animals are injected with indium-111-DTPA without antibody complex, the radioactive drug can sustain only for 1 hour in the abdominal organs. However, the indium-111-DTPA-YKL-40 antibody complex of the present disclosure starts to accumulate in the tumor site after four hours of injection, and the accumulation of the radioactive drug in the tumor becomes more significant along with time. The accumulation of the radioactive drug can at least last for 24 hours as shown in the results. The SPECT/CT images clearly indicate that the antibody complex drug can be eliminated through the gastrointestinal tract after being metabolized by the liver. The data obtained from the experiment indicates that the radiolabeled indium-111-DTPA-YKL-40 antibody complex can significantly accumulate in tumor cells overexpressing YKL-40, and thus can be used as a radio-diagnostic and imaging drug.

Figure 5B:
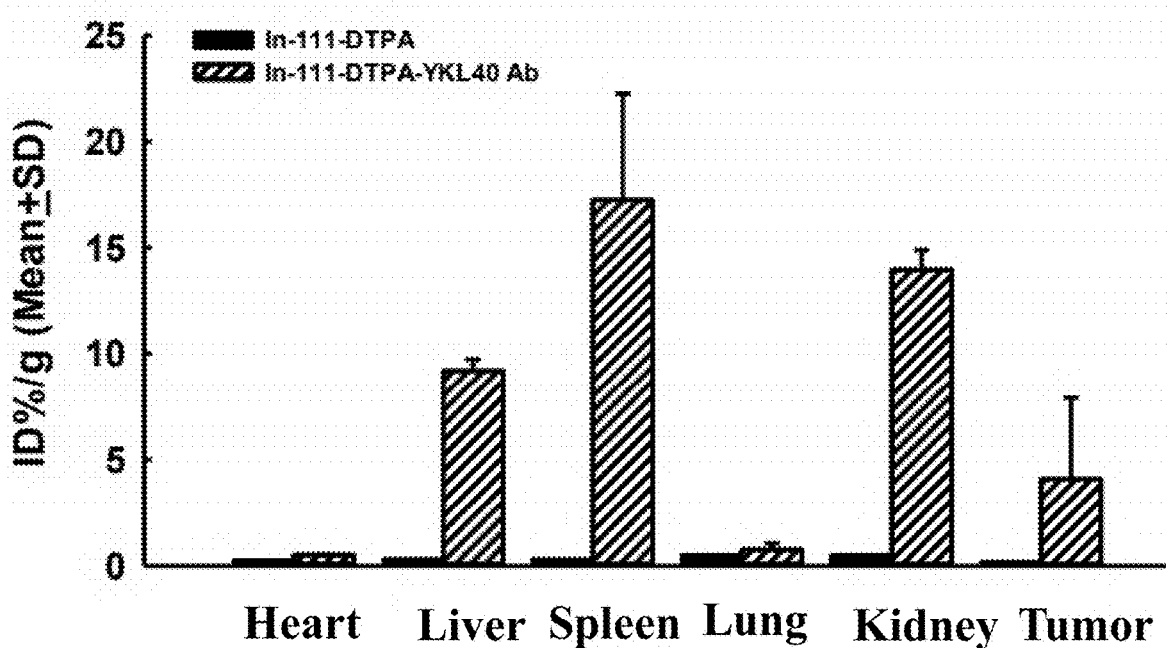

EXAMPLE 5: Analysis of the Distribution of Radioactive Antibody Complex Drugs in Organisms To verify the distribution of the indium-111-DTPA-YKL-40 antibody complex of the present disclosure in the main organs of the body, the biodistribution analysis is then performed. Please refer to FIG. 5B for the results. It is clearly demonstrated that the indium-111-DTPA-YKL-40 antibody complex is distributed mainly in spleen 17.2±5.0% ID/g, kidney 14.0±1.0% ID/g, and liver 9.2±0.5% ID/g, and the accumulation in the tumor site is 4.1±3.8% ID/g.

EXAMPLE 6: Radioactive Lutetium-177 Labeled DTPK-YKL-40 Antibody Complex Drug Inhibits the Growth of Tumors Overexpressing YKL-40

In order to test the clinical applicability of the disclosed DTPA-YKL-40 antibody complex as a radioactive antibody complex drug for targeted therapy, in the further experiments, this radiotherapy drug is used for the treatment of tumor-carried mice, and measure the change of tumor size after treated for various time period. Please refer to FIG. 6 for results. Seven days after tumor injection, the experimental animals begin to receive normal saline (the control group), free lutetium-177-DTPA, and the radiotherapy drug lutetium-177-DTPA-YKL-40 antibody complex. After 17 days of continuous treatments, the tumor volume of the treatment groups have reduced by 47%-61% compared with the control group of the normal saline group (2862.9±377.8 mm3 for the normal saline group, 3176.5±553.5 mm3 for the free lutetium-177-DTPA group, and 1528.1±369.5 mm3 for the tumor radiotherapy drug (i.e. lutetium-177-DTPA-YKL40 antibody complex) treatment group). The tumor volumes have significantly reduced for the experimental animals receiving the tumor radiotherapy drug (radiolabeled antibody complex) group, and smaller than the control group and the free lutetium-177-DTPA group, and the result of the analysis is statistically significant (p=0.01). To conclude, the above research evidences clearly indicate that the DPTA-YKL-40 antibody complex of the disclosure can significantly inhibit the growth of tumors overexpressing YKL-40, and thus can be used as an effective targeted radiotherapy drug to provide effective treatment for cancers.

The specific embodiments disclosed in the specification are not intended to limit the scope of the present invention or claims. Any other equivalent modifications or changes without departing from the spirit and scope of the instant disclosure should be included in the appended patent application scope.

What is claimed is:

1. An isolated neutralizing antibody that specifically binding to YKL-40, wherein the isolated neutralizing antibody comprising:

a heavy chain variable region (VH) comprising a CDR1 domain comprising the amino acid sequence of GYTFPNYGMN (SEQ ID NO: 1), a CDR2 domain comprising the amino acid sequence of WINTYTGEP-TYTVDFKG (SEQ ID NO: 2), and a CDR3 domain comprising the amino acid sequence of ARSFYGTNGFDY (SEQ ID NO: 3); and a light chain variable region (VL) comprising a CDR1 domain comprising the amino acid sequence of KASENVGTYVS (SEQ ID NO: 4), a CDR2 domain comprising the amino acid sequence of GASNRYI (SEQ ID NO: 5), and a CDR3 domain comprising the amino acid sequence of GQSYSYPPT (SEQ ID NO: 6).

2. The isolated neutralizing antibody of claim 1, wherein the heavy chain variable region (VH) comprises the amino acid sequence of SEQ ID NO: 7; and the light chain variable region (VL) comprises the amino acid sequence of SEQ ID NO: 8.

3. A nucleic acid molecule encoding the isolated neutralizing antibody of claim 1.

4. A vector comprising the nucleic acid molecule of claim 3.

5. A host cell comprising the vector of claim 4.

6. An antibody complex, comprising the isolated neutralizing antibody of claim 1 conjugated with a metal chelating group, wherein the metal chelating group is 1,4,7-triazcyclononane-N,N',N"-triacetic acid (NOTA), 1,4,7,10-tetraaza-cyclododecane-1,4,7, 10-tetraacetic acid (DOTA), tetraaza-cyclododecane-1-ethyl, diethylenetriaminepentaacetic acid (DTPA), 1,4,8,11-tetraazacyclotetradecane-N,N',N",N'"-tetraacetic acid (TETA), 1, 4,7-triazcyclononane phosphinic acid (TRAP) or ethylenediaminetetraacetic acid (EDTA).

7. The antibody complex of claim 6, wherein the metal chelating group is diethylenetriaminepentaacetic acid (DTPA).

8. The antibody complex of claim 6, further comprising a radioactive metal nuclide labeled on the antibody complex, wherein the radioactive metal nuclide is indium-111, lutetium-177, actinium-255, gallium-68, Gallium-67, Yttrium-90 or Copper-64.

9. The antibody complex of claim 8, wherein the radioactive metal nuclide is indium-111.

10. The antibody complex of claim 8, wherein the radioactive metal nuclide is lutetium-177.

11. The antibody complex of claim 8, wherein the radioactive metal nuclide is actinium-255.

12. A contrast agent comprising the antibody complex of claim 8 and a contrast excipient.

13. A pharmaceutical composition comprising the antibody complex of claim 8.

14. A method of treating a cancer overexpressing YKL-40, comprising administrating the antibody complex of claim 8.

15. The method of claim 14, wherein the cancer is selected from the group consisting of: breast cancer, liver cancer, prostate cancer, brain cancer, astrocytoma, ovarian cancer, endometrial cancer, lung cancer, and gastrointestinal cancer.

16. The method of claim 15, wherein the cancer is epithelial ovarian cancer.

17. A method of diagnosing a cancer overexpressing YKL-40, comprising administrating the antibody complex of claim 8.

18. The method of claim 17, wherein the cancer is selected from the group consisting of: breast cancer, liver cancer, prostate cancer, brain cancer, astrocytoma, ovarian cancer, endometrial cancer, lung cancer, and gastrointestinal cancer.

19. The method of claim 18, wherein the cancer is epithelial ovarian cancer.

* * * * *

```
                           SEQUENCE LISTING

Sequence total quantity: 8
SEQ ID NO: 1              moltype = AA  length = 10
FEATURE                   Location/Qualifiers
REGION                    1..10
                          note = recombinant YKL-40 neutralizing antibody
source                    1..10
                          mol_type = protein
                          organism = synthetic construct
SEQUENCE: 1
GYTFPNYGMN                                                            10

SEQ ID NO: 2              moltype = AA  length = 17
FEATURE                   Location/Qualifiers
REGION                    1..17
                          note = recombinant YKL-40 neutralizing antibody
source                    1..17
                          mol_type = protein
                          organism = synthetic construct
SEQUENCE: 2
WINTYTGEPT YTVDFKG                                                    17

SEQ ID NO: 3              moltype = AA  length = 12
FEATURE                   Location/Qualifiers
REGION                    1..12
                          note = recombinant YKL-40 neutralizing antibody
source                    1..12
                          mol_type = protein
                          organism = synthetic construct
SEQUENCE: 3
ARSFYGTNGF DY                                                         12

SEQ ID NO: 4              moltype = AA  length = 11
FEATURE                   Location/Qualifiers
REGION                    1..11
                          note = recombinant YKL-40 neutralizing antibody
source                    1..11
                          mol_type = protein
                          organism = synthetic construct
SEQUENCE: 4
KASENVGTYV S                                                          11

SEQ ID NO: 5              moltype = AA  length = 7
FEATURE                   Location/Qualifiers
REGION                    1..7
                          note = recombinant YKL-40 neutralizing antibody
source                    1..7
                          mol_type = protein
                          organism = synthetic construct
SEQUENCE: 5
GASNRYI                                                               7

SEQ ID NO: 6              moltype = AA  length = 9
FEATURE                   Location/Qualifiers
REGION                    1..9
                          note = recombinant YKL-40 neutralizing antibody
source                    1..9
                          mol_type = protein
                          organism = synthetic construct
SEQUENCE: 6
GQSYSYPPT                                                             9

SEQ ID NO: 7              moltype = AA  length = 119
FEATURE                   Location/Qualifiers
REGION                    1..119
                          note = recombinant YKL-40 neutralizing antibody
source                    1..119
                          mol_type = protein
                          organism = synthetic construct
SEQUENCE: 7
QIQLVQSGPE LKKPGETVRI SCKASGYTFP NYGMNWVKQA PGKGLKWMGW INTYTGEPTY  60
TVDFKGQFAF SLETSASTAY LQINNLKNED TATYFCARSF YGTNGFDYWG QGTTLTVSS   119

SEQ ID NO: 8              moltype = AA  length = 107
```

-continued

```
FEATURE          Location/Qualifiers
REGION           1..107
                 note = recombinant YKL-40 neutralizing antibody
source           1..107
                 mol_type = protein
                 organism = synthetic construct
SEQUENCE: 8
NIVMTQSPKS MSMSVGERVT LSCKASENVG TYVSWYQQKP EQSPKLVIYG ASNRYIGVPD   60
RFTGSGSATD FTLTISSVEA EDLADYHCGQ SYSYPPTFGG GTKLEIK              107
```